United States Patent
DeLuca et al.

(10) Patent No.: US 8,445,468 B2
(45) Date of Patent: May 21, 2013

(54) (20S,22E)-2-METHYLENE-19-NOR-22-ENE-1α,25-DIHYDROXYVITAMIN $D_3$

(75) Inventors: Hector F. DeLuca, Deerfield, WI (US); Pawel Grzywacz, Madison, WI (US); Lori A. Plum, Arena, WI (US); Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/895,390

(22) Filed: Sep. 30, 2010

(65) Prior Publication Data

US 2011/0086824 A1    Apr. 14, 2011

Related U.S. Application Data

(60) Provisional application No. 61/248,120, filed on Oct. 2, 2009.

(51) Int. Cl.
*A61K 31/593*    (2006.01)
*C07C 401/00*    (2006.01)

(52) U.S. Cl.
USPC .......................................... 514/167; 552/653

(58) Field of Classification Search
USPC .......................................... 514/167; 552/653
See application file for complete search history.

(56) References Cited

U.S. PATENT DOCUMENTS

| | | | |
|---|---|---|---|
| 7,232,810 B2 * | 6/2007 | DeLuca et al. | 514/167 |
| 7,241,748 B2 * | 7/2007 | DeLuca et al. | 514/167 |
| 7,241,752 B2 * | 7/2007 | DeLuca et al. | 514/167 |
| 7,241,909 B2 * | 7/2007 | DeLuca et al. | 552/653 |
| 7,528,122 B2 * | 5/2009 | DeLuca et al. | 514/167 |
| 7,741,314 B2 * | 6/2010 | DeLuca et al. | 514/167 |
| 7,803,789 B2 * | 9/2010 | Deluca et al. | 514/167 |
| 8,114,859 B2 * | 2/2012 | DeLuca et al. | 514/167 |
| 2006/0183716 A1 | 8/2006 | DeLuca et al. | |

FOREIGN PATENT DOCUMENTS

WO    2005/027928    3/2005

OTHER PUBLICATIONS

Sicinski, R. et al, "New 1alpha-25-Dihydroxy-19norvitamin D3 Compounds of High Biological Activity: Synthesis and Biological Evaluation of 2-Hydroxymethyl, 2-Methyl, and 2-Methylene Analogues", Journal of Medicinal Chemistry, American Chemical Society, Washington, US, vol. 41, 1998.
International Search Report and Written Opinion, PCT International Application No. PCT/US2010/050956, mailed Mar. 31, 2011.

* cited by examiner

*Primary Examiner* — Sabiha N Qazi
(74) *Attorney, Agent, or Firm* — Andrus, Sceales, Starke & Sawall, LLP

(57) ABSTRACT

This invention discloses (20S,22E)-2-methylene-19-nor-22-ene-1α,25-dihydroxyvitamin $D_3$ analogs, and specifically (20S,22E)-2-methylene-19-nor-22-ene-1α,25-dihydroxyvitamin $D_3$, and pharmaceutical uses therefor. This compound exhibits significant vitamin D receptor binding activity and transcription activity as well as pronounced activity in arresting the proliferation of undifferentiated cells and inducing their differentiation to the monocyte thus evidencing use as an anti-cancer agent, especially for the treatment or prevention of leukemia, colon cancer, breast cancer, skin cancer or prostate cancer.

20 Claims, 5 Drawing Sheets

HL-60 Cell Differentiation $EC_{50}$: $1,25(OH)_2D_3 = 2 \times 10^{-9}$ M
N-23 $= 1 \times 10^{-10}$ M

(20S,22E)-2-METHYLENE-19-NOR-22-ENE-1α,25-DIHYDROXYVITAMIN D₃

BACKGROUND OF THE INVENTION

This invention relates to vitamin D compounds, and more particularly to (20S,22E)-2-Methylene-19-nor-22-ene-1α, 25-dihydroxyvitamin $D_3$ analogs and their pharmaceutical uses.

The natural hormone, 1α,25-dihydroxyvitamin $D_1$ and its analog in ergosterol series, i.e. 1α,25-dihydroxyvitamin $D_2$ are known to be highly patent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett, 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int, Suppl. 1, 190 (1993); Posner et al., J. Org. Chem. 59, 7855 (1994), and J. Org. Chem. 60, 4617 (1995)), as have analogs with a cyclopropyl group in the side chain (e.g. MC-903 known as calcipotriene and described in Nishii et al U.S. Pat. No. 5,063,221).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α, 25-dihydroxyvitamin $D_3$. Their biological activities make these compounds excellent candidates for a variety of pharmaceutical uses, as set forth in the '352, '861 and '622 patents.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

19-nor vitamin D compounds substituted at the carbon-2 position of ring A with an alkyl group such as methyl, or an alkylidene group such as methylene, and having a side chain lacking one or more of the standard vitamin $D_3$ substitutents, are also known, and have been proposed for various pharmacological uses. For example, numerous 2α-methyl-19,26,27-trinor analogs are described in U.S. Pat. No. 7,241,749 and in U.S. Pat. No. 7,241,909, and numerous 2-methylene-19,26, 27-trinor analogs are described in U.S. Pat. No. 7,244,719. In addition, 2α-methyl-19-nor-(20S)-1α-hydroxy-bishomopregnacalciferol is described in published U.S. Application No. 2007/0254857, and numerous 2-methylene-19,26-dinor vitamin D analogs are described in published U.S. Application No. 2007/0191317 and in published U.S. Application No. 2007/0191316.

SUMMARY OF THE INVENTION

The present invention is directed toward (20S,22E)-2-Methylene-19-nor-22-ene-1α,25-dihydroxyvitamin $D_3$ analogs, their biological activity, and various pharmaceutical uses for these compounds. These new vitamin compounds not known heretofore are the 19-nor-vitamin D analogs having a methylene group at the 2-position (C-2), a hydroxyl substituent attached to the 25-position (C-25) in the side chain, the methyl group normally located at the 21 position (C-21) in the side chain in its epi or S-configuration, and a double bond located between carbon atoms 22 and 23 (C-22 and C-23) in the side chain. The preferred vitamin D analog is (20S,22E)-2-Methylene-19-nor-22-ene-1α,25-dihydroxyvitamin $D_3$ (hereinafter referred to as "N-23").

Structurally these (20S,22E)-2-Methylene-19-nor-22-ene-1α,25-dihydroxyvitamin $D_3$ analogs are characterized by the general formula I shown below:

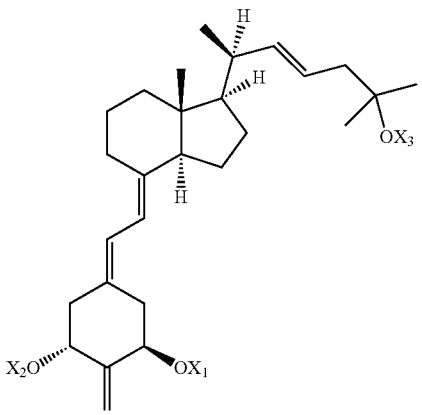

where $X_1$, $X_2$ and $X_3$, which may be the same or different, are each selected from hydrogen or a hydroxy-protecting group. The preferred analog is (20S,22E)-2-Methylene-19-nor-22-ene-1α,25-dihydroxyvitamin $D_3$ which has the following formula Ia:

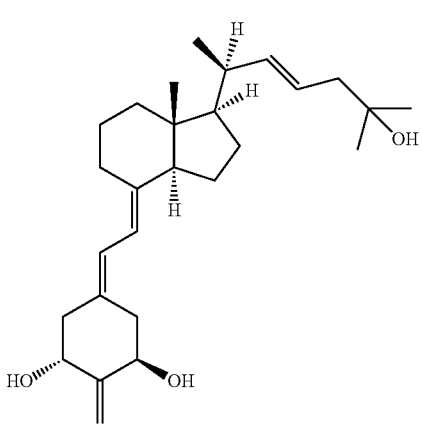

The above compounds I, particularly Ia, exhibit a desired, and highly advantageous, pattern of biological activity. These compounds are characterized by relatively high binding to the vitamin D receptor, which is about the same as that of the native hormone 1α,25-dihydroxyvitamin $D_3$. These compounds are more potent (one log) in causing cellular differentiation and in increasing 24-OHase gene expression compared to 1,25$(OH)_2D_3$. These compounds also have less ability to promote intestinal calcium transport in vivo than 1,25$(OH)_2D_3$, especially at the recommended lower doses. They would be classified as having lower activity and thus lower potency in vivo in stimulating intestinal calcium transport activity, as compared to that of 1α,25-dihydroxyvitamin $D_3$. These compounds I, and particularly Ia, also have significant ability to mobilize calcium from bone, and they would be classified as being slightly more effective in bone calcium mobilizing activity as compared to 1α,25-dihydroxyvitamin $D_3$.

The above compounds I, and particularly Ia, are characterized by relatively high cell differentiation activity and in promoting transcription of the 24-hydroxylase gene. Thus, because these compounds are more potent than the native hormone in causing cellular differentiation and transcription and are less potent in causing intestinal calcium transport, they have potential as an anti-cancer agent, especially for the prevention or treatment of leukemia, colon cancer, breast cancer, skin cancer and prostate cancer.

One or more of the compounds may be present in a composition to treat the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIG. 1 is a graph illustrating the relative activity of N-23 and 1,25$(OH)_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of N-23 and 1,25$(OH)_2D_3$;

FIG. 3 is a graph illustrating the in vitro transcription activity of 1,25$(OH)_2D_3$ as compared to N-23;

FIG. 4 is a graph illustrating the bone calcium mobilization activity of 1,25$(OH)_2D_3$ as compared to N-23 in a group of animals; and FIG. 5 is a graph illustrating the intestinal calcium transport activity of 1,25$(OH)_2D_3$ as compared to N-23 in a group of animals.

Figure 1:
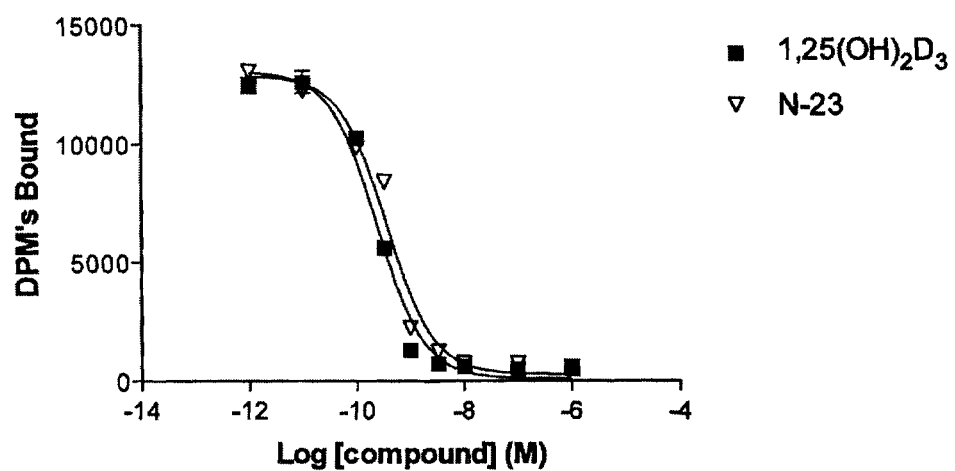
FIGS. 1-5 illustrate various biological activities of (20S, 22E)-2-Methylene-19-nor-22-ene-1α,25-dihydroxyvitamin $D_3$, hereinafter referred to as "N-23", as compared to the native hormone 1α,25-dihydroxyvitamin $D_3$, hereinafter "1,25$(OH)_2D_3$."

DETAILED DESCRIPTION OF THE INVENTION (20S,22E)-2-Methylene-9-nor-22-ene-1α,25-dihydroxyvitamin $D_3$ (referred to herein as "N-23") a 19-nor vitamin D analog which is characterized by the presence of a methylene substituent at the carbon 2 (C-2), a hydroxyl substituent attached to the 25-position (C-25) in the side chain, the methyl group normally located at the 21 position (C-21) in the side chain in its epi or S-configuration, and a double bond located between carbon atoms 22 and 23 (C-22 and C-23) in the side chain, was synthesized and tested. Such vitamin D analog seemed an interesting target because the relatively small methylene group at the C-2 position should not interfere with binding to the vitamin D receptor, Structurally, this 19-nor analog is characterized by the general formula Ia previously illustrated herein, and its pro-drug (in protected hydroxy form) is characterized by general formula I previously illustrated herein.

The preparation of (20S,22E)-2-Methylene-19-nor-22-ene-1α,25-dihydroxyvitamin $D_3$ analogs having the structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1, C-3 and C-25 in the latter compound (see Schemes 1 and 2 herein):

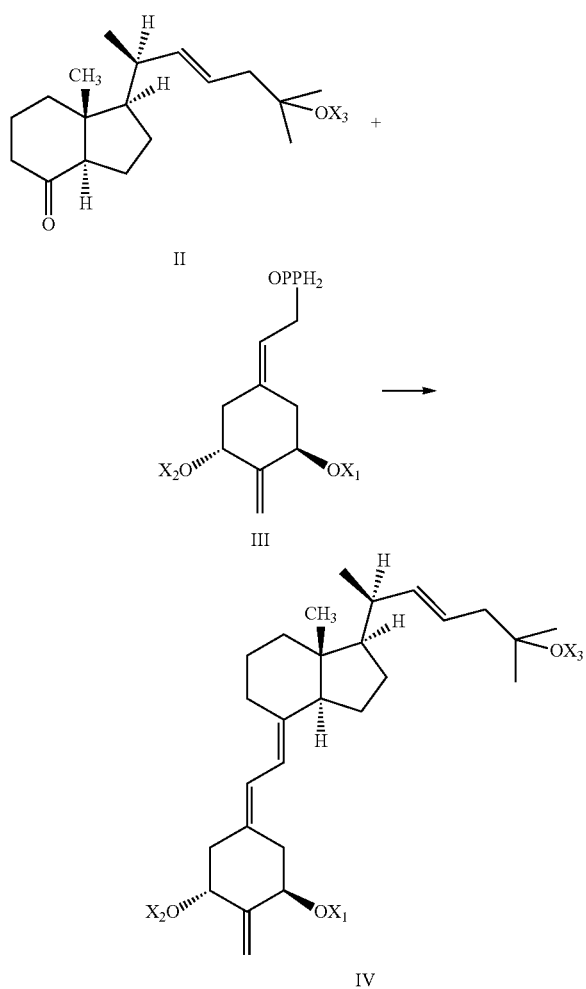

In the structures II, III and IV, groups $X_1$, $X_2$ and $X_3$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown in Schemes 1 and 2 herein (see the preparation of compound N-23).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,843,928 entitled "2-Alkylidene-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O."Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

More specifically, reference should be made to the following illustrative example and description as well as to Schemes 1 and 2 herein for a detailed illustration of the preparation of compound N-23.

In this example specific products identified by Arabic numerals (1, 2, 3) refer to the specific structures so identified in the Schemes 1 and 2.

EXAMPLES

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuterochloroform. Chemical shifts (δ) are reported downfield from internal Me$_4$Si (δ 0.00). Mass spectra were recorded at 70 eV on a Kratos DS-50 TC instrument equipped with a Kratos MS-55 data system. Samples were introduced into the ion source maintained at 120-250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer.

Example 1

Preparation of (8S,20S)-des-A,B-20-(hydroxymethyl)-pregnan-8-ol (1)

Ozone was passed through a solution of vitamin D$_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with $NaBH_4$ (0.75 g, 20 mmol). After 20 min the second portion of $NaBH_4$ (0.75 g, 20 mmol) was added and the mixture was allowed to warm to room temperature. The third portion of $NaBH_4$ (0.75 g, 20 mmol) was then added and the reaction mixture was stirred for 18 h. The reaction was quenched with water (40 mL) and the solution was concentrated under reduced pressure. The residue was extracted with ethyl acetate and the combined organic phases were washed with 1 M aq. HCl, saturated aq. $NaHCO_3$, dried ($Na_2SO_4$) and concentrated under reduced pressure. The residue was chromatographed on silica gel with hexane/ethyl acetate (75:25) to give the diol 1 (1.21 g, 75% yield) as white crystals:

m.p. 106-108° C.; $[\alpha]_D$+30.2° (c 1.46, $CHCl_3$); $^1$H NMR (400 MHz, $CDCl_3$) δ 4.08 (1H, d, J=2.0 Hz, 8α-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-$H_3$), 0.956 (3H, s, 18-$H_3$); $^{13}$C NMR (100 MHz) δ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, $M^+$), 194 (34, $M^+-H_2O$), 179 (33, $M^+-H_2O-CH_3$), 163 (18, $M^+CH_2OH-H_2O$), 135 (36), 125 (54), 111 (100), 95 (63), 81 (67); exact mass calculated for $C_{13}H_{22}O$ ($M^+-H_2O$) 194.1671, found 194.1665.

Preparation of (8S,20S)-des-A,B-8-benzoyloxy-20-(hydroxymethyl)-pregnane (2)

Benzoyl chloride (2.4 g, 2 mL, 17 mmol) was added to a solution of the diol 1 (1.2 g, 5.7 mmol) and DMAP (30 mg, 0.2 mmol) in anhydrous pyridine (20 mL) at 0° C. The reaction mixture was stirred at 4° C. for 24 h, diluted with methylene chloride (100 mL), washed with 5% aq. HCl, water, saturated aq. $NaHCO_3$, dried ($Na_2SO_4$) and concentrated under reduced pressure. The residue (3.39 g) was treated with a solution of KOH (1 g, 15.5 mmol) in anhydrous ethanol (30 mL) at room temperature. After stirring of the reaction mixture for 3 h, ice and 5% aq. HCl were added until pH=6. The solution was extracted with ethyl acetate (3×50 mL) and the combined organic phases were washed with saturated aq. $NaHCO_3$, dried ($Na_2SO_4$) and concentrated under reduced pressure. The residue was chromatographed on silica gel with hexane/ethyl acetate (75:25) to give the alcohol 2 (1.67 g, 93% yield) as a colorless oil:

$[\alpha]_D$+56.0 (c 0.48, $CHCl_3$); $^1$H NMR (400 MHz, $CDCl_3$ αTMS) δ 8.08-8.02 (2H, m, o-$H_{Bz}$), 7.59-7.53 (1H, m, p-$H_{Bz}$), 7.50-7.40 (2H, m, m-$H_{Bz}$), 5.42 (1H, d, 2.4 Hz, 8α-H), 3.65 (1H, dd, J=10.5, 3.2 Hz, 22-H), 3.39 (1H, dd, J=10.5, 6.8 Hz, 22-H), 1.08 (3H, d, J=5.3 Hz, 21-$H_3$), 1.07 (3H, s, 18-$H_3$); $^{13}$C NMR (125 MHz) δ 166.70 (s, C=O), 132.93 (d, p-$C_{Bz}$), 130.04 (s, i-$C_{Bz}$), 129.75 (d, o-$C_{Bz}$), 128.57 (d, m-$C_{Bz}$), 72.27 (d, C-8), 67.95 (t, C-22), 52.96 (d), 51.60 (d), 42.15 (s, C-13), 39.98 (t), 38.61 (d), 30.73 (t), 26.81 (t), 22.91 (t), 18.20 (t), 16.87 (q, C-21), 13.81 (q, C-18); MS (EI) m/z 316 (5, $M^+$), 301 (3, $M^+-Me$), 299 (1, $M^+-OH$), 298 (2, $M^+-H_2O$), 285 (10, $M^+-CH_2OH$), 257 (6), 230 (9), 194 (80), 135 (84), 105 (100); exact mass calculated for $C_{20}H_{28}O_3$ 316.2038, found 316.2019.

Preparation of (8S,20S)-des-A,B-8-benzoyloxy-20-formyl-pregnane (3)

Sulfur trioxide pyridine complex (1.94 g, 12.2 mmol) was added to a solution of the alcohol 2 (640 mg, 2.03 mmol), triethylamine (1.41 mL, 1.02 g, 10.1 mmol) in anhydrous methylene chloride (10 mL) and anhydrous DMSO (2 mL) at 0° C. The reaction mixture was stirred under argon at 0° C. for 1 h and then concentrated. The residue was diluted with ethyl acetate, washed with brine, dried ($Na_2SO_4$) and concentrated. The residue was purified by column chromatography on silica gel with hexane/ethyl acetate (95:5) to give the aldehyde 3 (529 mg, 83% yield) as an oil:

$[\alpha]_D$+63.1 (c 5.85, $CHCl_3$); $^1$H NMR (400 MHz, $CDCl_3$+ TMS) δ 9.60 (1H, d, J=3.1 Hz, CHO, 8.05 (2H, m, o-$H_{Bz}$), 7.57 (1H, m, p-$H_{Bz}$), 7.45 (2H, m, m-$H_{Bz}$), 5.44 (1H, s, 8α-H), 2.39 (1H, m, 20-H), 2.03 (2H, dm, J=11.5 Hz), 1.15 (3H, d, J=6.9 Hz, 21-$H_3$), 1.10 (3H, s, 18-$H_3$); $^{13}$C NMR (100 MHz) δ 204.78 (d, CHO), 166.70 (s, C=O), 132.78 (d, p-Bz), 130.69 (s, i-Bz), 129.50 (d, o-Bz), 128.38, (d, m-Bz), 71.66 (d, C-8), 51.30 (d), 50.95 (d), 49.20 (d), 42.38 (s, C-13), 39.62 (t), 30.47 (t), 25.99 (t), 22.92 (t), 17.92 (t), 13.90 (q), 13.35 (q); MS (EI) m/z 314 (1, $M^+$), 299 (0.5, $M^+$-Me), 286 (1, $M^+$-CO), 285 (5, $M^+$-CHO), 257 (1, $M^+C_3H_5O$), 209 (10, $M^+$-PhCO), 192 (38), 134 (60), 105 (100), 77 (50); exact mass calculated for $C_{20}H_{26}O_3$ 314.1882, found 314.1887.

Preparation of (8S,20R)-des-A,B-8-benzoyloxy-20-(hydroxymethyl)-pregnane (4)

The aldehyde 3 (364 mg, 1.12 mmol) was dissolved in methylene chloride (15 mL) and a 40% aq. n-$Bu_4NOH$ solution (1.47 mL, 1.45 g, 2.24 mmol) was added. The resulting mixture was stirred under argon at room temperature for 16 h, diluted with methylene chloride (20 mL), washed with water, dried ($Na_2SO_4$) and concentrated under reduced pressure. A residue was chromatographed on silica gel with hexane/ethyl acetate (95:5) to afford a mixture of aldehyde 3 and its 20-epimer (292 mg, 80% yield) in ca. 1:2 ratio (by $^1$H NMR).

This mixture of aldehydes (292 mg, 0.9 mmol) was dissolved in THF (5 mL) and $NaBH_4$ (64 mg, 1.7 mmol) was added, followed by a dropwise addition of ethanol (5 mL). The reaction mixture was stirred at room temperature for 30 min and it was quenched with a saturated aq. $NH_4Cl$ solution. The mixture was extracted with ether (3×20 mL) and the combined organic phase was washed with water, dried ($Na_2SO_4$) and concentrated under reduced pressure. The residue was chromatographed on silica gel with hexane/ethyl acetate (96:4→80:20) to give the desired, pure (20R)-alcohol 4 (160 mg, 55% yield) as an oil and a mixture of 4 and its 20-epimer 2 (126 mg, 43% yield) in ca. 1:3 ratio (by $^1$H NMR).

$[\alpha]_D$+50.1 (c 1.09, $CHCl_3$); $^1$H NMR (400 MHz, $CDCl_3$+ TMS) δ 8.05 (2H, m, o-$H_{Bz}$), 7.55 (1H, m, p-$H_{Bz}$), 7.44 (2H, m, m-$H_{Bz}$), 5.41 (1H, s, 8α-H), 3.77 (1H, dd, J=10.4, 3.3 Hz, 22-H), 3.45 (1H, dd, J=10.4, 7.4 Hz, 22-H), 1.067 (3H, s, 18-$H_3$), 0.973 (3H, d, J=6.6 Hz, 21-$H_3$); $^{13}$C NMR (100 MHz) δ 166.36 (s, C=O), 132.61 (d, p-$C_{Bz}$), 130.63 (s, i-$C_{Bz}$), 129.39 (d, o-$C_{Bz}$), 128.23 (d, m-$C_{Bz}$), 71.97 (d, C-8), 66.42 (t, C-22), 52.65 (d), 51.38 (d), 41.58 (s, C-13), 39.16 (t), 37.45 (d), 30.38 (t), 26.29 (t),22.35 (t), 17.89 (t), 16.42 (q, C-21), 13.78 (q, C-18); MS (EI) m/z 316 (16, $M^+$), 301 (5, $M^+$-Me), 299 (2, $M^+$-OH), 298 (3, $M^+-H_2O$), 285 (9, $M^+-CH_2OH$), 257 (5), 242 (11), 230 (8), 194 (60), 147 (71), 105 (100); exact mass calculated for $C_{20}H_{28}O_3$ 316.2038, found 316.2050.

Preparation of (8S,20R)-des-A,B-8-benzoyloxy-20-formyl-pregnane (5)

Sulfur trioxide pyridine complex (258 mg, 1.62 mmol) was added to a solution of the alcohol 4 (111 mg, 0.35 mmol), triethylamine (188)μL, 136 mg, 1.35 mmol) in anhydrous methylene chloride (5 mL) and anhydrous DMSO (1 mL) at 0° C. The reaction mixture was stirred under argon at 0° C. for 1 h and then concentrated. The residue was diluted with ethyl acetate, washed with brine, dried ($Na_2SO_4$) and concentrated. The residue was purified by column chromatography on silica gel with hexane/ethyl acetate (95:5) to give the aldehyde 5 (93 mg, 85% yield) as an oil:

$[\alpha]_D$+28.8 (c 0.88, $CHCl_3$); $^1$H NMR (500 MHz, $CDCl_3$) δ 9.55 (1H, d, J=5.0 Hz, CHO), 8.02 (2H, m, o-$H_{Bz}$), 7.54 (1H, m, p-$H_{Bz}$), 7.43 (2H, m, m-$H_{Bz}$), 5.42 (1H, s, 8α-H), 2.35 (1H, m, 20-H), 2.07 (1H, m), 1.87 (1H, m), 1.05 (3H, s, 18-$H_3$), 1.04 (3H, d, J=7.8 Hz, 21-$H_3$); $^{13}$C NMR (125 MHz) δ 205.51 (d, CHO), 166.34 (s, C=O), 132.76 (d, p-$C_{Bz}$), 130.62 (s, i-$C_{Bz}$), 129.47 (d, o-$C_{Bz}$), 128.35, (d, m-$C_{Bz}$), 71.52 (d, C-8), 52.08 (d), 51.08 (d), 48.40 (d), 41.55 (s, C-13), 38.54 (t), 30.41 (t), 25.28 (t), 22.08 (t), 17.68 (t), 14.49 (q), 13.38 (q); MS (EI) m/z 314 (2, $M^+$), 285 (3, $M^+$-CHO), 209 (8, $M^+$PhCO), 192 (30, $M^+$PhCOOH), 177 (14), 134 (45), 105 (100), 77 (50); exact mass calculated for $C_{19}H_{25}O_2$ ($M^+$-CHO) 285.1855, found 285.1849.

Preparation of (8S,20S)-des-A,B-8-benzoyloxy-20-[4'-hydroxy-4'-methyl-pent-(1'E)-en-yl]-pregnane (7)

n-Butyllithium (1.61 M, 1.38 mL, 2.22 mmol) was added to a stirred suspension of the phosphonium salt 6 (476 mg, 1.11 mmol) in anhydrous THF (6 mL) at −20° C. The solution turned orange. After 1 h a precooled (−20° C.) solution of the aldehyde 5 (93 mg, 0.30 mmol) in anhydrous THF (1+0.5 mL) was added and the reaction mixture was stirred at −20° C. for 3 h and at room temperature for 18 h. The reaction was quenched with water and the mixture was extracted with ethyl acetate. Combined organic phases were washed with brine, dried ($Na_2SO_4$) and evaporated. The residue was chromatographed on silica gel with hexane/ethyl acetate (95:5, then 90:10) to give the product 7 (52 mg, 45% yield):

$[\alpha]_D$-25.1 (c 2.5, $CHCl_3$); $^1$H NMR (500 MHz, $CDCl_3$) δ 8.04 (2H, m, o-$H_{Bz}$), 7.55 (1H, m, p-$H_{Bz}$), 7.44 (2H, m, m-$H_{Bz}$), 5.42 (3H, m, 8α-H, 22-H, 23-H), 1.22 (6H, 26,27-$H_6$), 1.04 (3H, s, 18-$H_3$), 0.94 (3H, d, J=6.6 Hz, 21-$H_3$); $^{13}$C NMR (125 MHz) δ 166.41 (s, C=O), 141.34 (d, C-22), 132.64 (d, p-$C_{Bz}$), 130.83 (s, i-$C_{Bz}$), 129.50 (d, o-$C_{Bz}$), 128.29 (d, m-$C_{Bz}$), 122.86 (d, C-23), 72.06 (d, C-8), 70.68 (s, C-25), 56.30 (d), 51.46 (d), 46.92 (t), 41.91 (s, C-13), 40.23 (d), 39.33 (t), 30.57 (t), 29.12 and 29.11 (each q, C-26 and C-27), 26.83 (t), 22.49 (t), 21.57 (q, C-21), 17.78 (t), 13.80 (q, C-18); MS (EI) m/z no $M^+$, 366 (5, $M^+$-$H_2O$), 326 (38, $M^+$-$C_3H_6O$), 284 (38, $M^+$-$C_6H_{12}O$), 204 (54), 162 (88), 135 (93), 121 (53), 105 (100); exact mass calculated for $C_{25}H_{36}O_3Na$ ($MNa^+$) 407.2562, found 407.2561.

Preparation of (8S,20S)-des-A,B-8-benzoyloxy-20-[4'-(tert-butyldimethylsilyloxy)-4'-methyl-pent-(1'E)-en-yl]-pregnane (8)

tert-Butyldimethylsilyl trifluoromethanesulfonate (32 μL, 37 mg, 0.14 mmol) was added to a solution of the alcohol 7 (52 mg, 0.14 mmol) and 2,6-lutidine (33 μL, 30 mg, 0.28 mmol) in anhydrous methylene chloride (3 mL) at −20° C. The mixture was stirred under argon at room temperature for 3 h. The reaction was quenched with water and extracted with methylene chloride. The combined organic phases were washed with brine, dried ($Na_2SO_4$) and concentrated under reduced pressure. The residue was chromatographed on silica gel with hexane and hexane/ethyl acetate (97:3) to give the product 8 (65 mg, 93%):

$[\alpha]_D$−21.2 (c 4.95, $CHCl_3$); $^1$H NMR (500 MHz, $CDCl_3$+ TMS) δ 8.05 (2H, m, o-$H_{Bz}$), 7.54 (1H, m, p-$H_{Bz}$), 7.43 (2H, m, m-$H_{Bz}$), 5.41 (2H, m, 8α-H and 23-H), 5.29 (1H, dd, J=15.4, 9.1 Hz, 22-H), 1.18 (6H, d, J=4.5 Hz, 26,27-$H_6$), 1.04 (3H, s, 18-$H_3$), 0.93 (3H, d, J=6.6 Hz, 21-$H_3$), 0.87 (9H, s, Si-t-Bu), 0.08 (6H, s, $SiMe_2$); $^{13}$C NMR (125 MHz) δ 166.43 (s, C=O), 139.10 (d, C-22), 132.62 (d, p-$C_{Bz}$), 130.91 (s, i-$C_{Bz}$), 129.53 (d, o-$C_{Bz}$), 128.30 (d, m-$C_{Bz}$), 124.39 (d, C-23), 73.72 (s, C-25), 72.14 (d, C-8), 56.44 (d), 51.52 (d), 48.29 (t), 41.94 (s, C-13), 40.30 (d), 39.28 (t), 30.63 (t), 29.76 and 29.65 (each q, C-26 and C-27), 26.88 (t), 25.83 (q, $SiCMe_3$), 22.56 (t), 21.53 (q, C-21), 18.04 (s, $SiCMe_3$), 17.82 (t), 13.68 (q, C-18), −2.04 (q, $SiMe_2$); MS (EI) m/z no $M^+$, 483 (5, $M^+$-$CH_3$), 441 (8, $M^+$-$C_4H_9$), 359 (2), 339 (5), 245 (6), 237 (9), 173 (100), 163 (36), 135 (38), 105 (54); exact mass calculated for $C_{31}H_{50}O_3SiNa$ ($MNa^+$) 521.3427, found 521.3450.

Preparation of (8S,20S)-des-A,B-20-[4'-(tert-butyldimethylsilyloxy)-4'-methyl-pent-(1'E)-en-yl]-pregnan-8-ol (9)

A solution of sodium hydroxide in ethanol (2.5M, 8 mL) was added to a stirred solution of the benzoate 8 (65 mg, 131 μmol) in anhydrous ethanol (20 mL) and the reaction mixture was refluxed for 21 h. The mixture was cooled to room temperature, neutralized with 5% aq. HCl and extracted with dichloromethane. Combined organic phases were washed with saturated aq. $NaHCO_3$, dried ($Na_2SO_4$) and evaporated. The residue was chromatographed on silica gel with hexane/ethyl acetate (97:3) to give the alcohol 9 (49 mg, 95% yield):

$[\alpha]_D$+1.1 (c 3.6, $CHCl_3$); $^1$H NMR (500 MHz, $CDCl_3$) δ 5.38 (1H, ddd, J=15.4, 7.9, 7.0 Hz, 23-H), 5.25 (1H, dd, J=15.4, 9.1 Hz, 22-H), 4.07 (1H, s, 8α-H), 2.10 (3H, m), 1.16 (6H, d, J=3.0 Hz, 26,27-$H_6$), 0.92 (3H, s, 18-$H_3$), 0.89 (3H, d, J=6.7 Hz, 2-$H_3$), 0.86 (9H, s, Si-t-Bu), 0.07 (6H, s, $SiMe_2$); $^{13}$C NMR (125 MHz) δ 139.15 (d, (C-22), 124.27 (d, C-23), 73.73 (s, C-25), 69.35 (d, C-8), 56.69 (d), 52.53 (d), 48.28 (t), 41.86 (s, C-13), 40.06 (d), 39.71 (t), 33.66 (t), 29.77 and 29.61 (each q, C-26 and C-27), 26.93 (t), 25.82 (q, $SiCMe_3$), 22.39 (t), 21.51 (q, C-21), 18.04 (s, $SiCMe_3$), 17.22 (t), 13.68 (q, C-18), −2.05 (q, $SiMe_2$); MS (EI) m/z $M^+$, 393 (0.5, $M^+$-H), 379 (5, $M^+$-$CH_3$), 337 (3, $M^+$-$C_4H_9$), 279 (6, $M^+$-t-$BuSiMe_2$), 255 (9), 237 (96), 193 (42), 173 (100), 157 (43), 135 (40), 115 (37); exact mass calculated for $C_{24}H_{46}O_2SiNa$ ($MNa^+$) 417.3165, found 417.3165.

Preparation of (20S)-des-A,B-20-[4'-tert-butyldimethylsilyloxy)-4'-methyl-pent-(1'E)-en-yl]-pregnan-8-one (10)

Molecular sieves A4 (0.6 g) were added to a solution of 4-methylmorpholine oxide (55 mg, 0.47 mmol) in dichloromethane (0.6 mL). The mixture was stirred at room temperature for 15 min and tetrapropylammonium perruthenate (8 mg, 23 μmol) was added, followed by a solution of alcohol 9 (28 mg, 71 μmol) in dichloromethane (300+250 μL). The resulting suspension was stirred at room temperature for 1 h. The reaction mixture was filtered through a Waters silica Sep-Pak cartridge (5 g) that was further washed with dichloromethane. After removal of the solvent the ketone 10 (27 mg, 97% yield) was obtained as a colorless oil:

$[\alpha]_D$-39.3 (c 1.35, $CHCl_3$); $^1$H NMR (400 MHz, $CDCl_3$) δ 5.42 (1H, ddd, J=15.4, 8.2, 7.0 Hz, 23-H), 5.28 (1H, dd, J=15.4, 9.1 Hz, 22-H), 2.42 (1H, dd, J=11.4, 7.6 Hz), 1.17 (6H, s, 26,27-$H_6$), 0.94 (3H, d, J=6.6 Hz, 21-$H_3$), 0.86 (9H, s, Si-t-Bu), 0.61 (3H, s, 18-$H_3$), 0.069 and 0.065 (each 3H, each s, each SiMe$_2$); $^{13}$C NMR (100 MHz) δ 212.10 (s, C=O), 138.69 (d, C-22), 124.97 (d, C-23), 73.65 (s, C-25), 61.91 (d), 56.57 (d), 50.03 (s, C-13), 48.23 (t), 41.03 (t), 40.44 (d), 38.28 (t), 29.79 and 29.62 (each q, C-26 and C-27), 27.21 (t), 25.79 (q, SiCMe$_3$), 23.93 (t), 21.52 (q, C-21), 18.97 (t), 18.03 (s, SiCMe$_3$), $\overline{12}$.49 (q, C-18), −2.06 (q, Si$\overline{\text{Me}}_2$); MS (EI) M/z no M$^+$, 377 (6, M$^+$-CH$_3$), 335 (26, M$^+$-t-$\overline{\text{Bu}}$), 253 (59), 209 (24), 173 (100), 161 (25), 133 (22); exact mass calculated for C$_{24}$H$_{44}$O$_2$SiNa (MNa$^+$) 415.3008, found 415.3018.

Preparation of (20S,22E)-2-Methylene-19-nor-22-ene-1α,25-dihydroxyvitamin D$_3$ (13)

To a solution of phosphine oxide 11 (67 mg, 115 μmol) in anhydrous THF (500 μL) at −20° C. was slowly added PhLi (1.83 M in di-n-butylether, 75 μL, 137 μmol) under argon with stirring. The solution turned deep orange. After 30 min the mixture was cooled to −78° C. and a precooled (−78° C.) solution of ketone 10 (26 mg, 66 μmol in anhydrous THF (300+300 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 12 (39.54 mg, 79% yield).

UV (in hexane) $\lambda_{max}$ 262.5, 253.0, 245.0 nm; $^1$H NMR (400 MHz, CDCl$_3$) δ 6.21 and 5.83 (each 1H, each d, J=11.1 Hz, 6- and 7-H), 5.38 (1H, ddd, J=15.4, 8.4, 6.8 Hz, 23-H), 5.29 (1H, dd, J=15.4, 8.7 Hz, 22-H), 4.97 and 4.92 (each 1H, each s, =CH$_2$), 4.42 (2H, m, 1β- and 3α-H), 2.81 (1H, dm, J=13.1 Hz, 9β-H), 2.52 (1H, dd, J=13.2, 5.8 Hz, 10α-H), 2.46 (1H, dd, J=12.7, 4.3 Hz, 4α-H), 2.33 (1H, dd. J=13.2, 2.4 Hz, 10β-H), 2.17 (1H, dd, J=12.7, 8.4 Hz, 4β-H), 1.16 (6H, s, 26,27-H$_6$), 0.93 (3H, d, J=6.4 Hz, 21-H$_3$), 0.895 (9H, s, Si-t-Bu), 0.865 (9H, s, Si-t-Bu), 0.855 (9H, s, Si-t-Bu), 0.518 (3H, s, 18-H$_3$), 0.0177 (3H, s, SiMe), 0.066 (9H, s, 3× SiMe), 0.047 (3H, s, SiMe), 0.025 (3H, s, SiMe); $^{13}$C NMR (100 MHz) δ 152.99 (s, C-2), 141.32 (s, C-8), 139.40 (d, C-22), 132.63 (s, C-5), 124.25 (d, C-23), 122.42 (d, C-6), 116.00 (d, C-7), 106.24 (t, =CH$_2$), 73.78 (s, C-25), 72.53 and 71.63 (each d, C-1 and C-3), 56.67 (d), 56.20 (d), 48.29 (t), 47.61 (t), 45.76 (s, C-13), 40.91 (d), 39.86 (t), 38.55 (t), 29.83 and 29.62 (each q, C-26 and C-27), 28.77 (t), 27.41 (t), 25.84 (q, 2× SiCMe$_3$), 25.78 (q, SiCMe$_3$), 23.23 (t), 22.11 (t), 21.57 (q, C-21), $\overline{18.25}$ (s, SiCMe$_3$), $\overline{18.16}$ (s, SiCMe$_3$), 18.07 (s, SiCMe$_3$), 12.11 (q, C-18$\overline{)}$, −2.04 (q, 2× Si$\overline{\text{Me}}$), −4.86 (q, 2× Si$\overline{\text{Me}}$), −4.90 (q, Si$\overline{\text{Me}}$), −5.10 (q, Si$\overline{\text{Me}}$); exact mass calculated for $\overline{\text{C}}_{45}$H$_{84}$O$_3$Si$_3$Na (MNa$^+$) 779.5626, found 779.5651.

The protected vitamin 12 (39.44 mg, 52 μmol) was dissolved in THF (5 mL) and acetonitrile (3 mL). A solution of aq. 48% HF in acetonitrile (1:9 ratio, 5 mL) was added at 0° C. and the resulting mixture was stirred at room temperature for 11 h. Saturated aq. NaHCO$_3$ solution was added and the reaction mixture was extracted with ethyl acetate. The combined organic phases were washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). An elution with hexane/ethyl acetate (75:25) gave the crude product 13 (18 mg). The vitamin 13 was further purified by straight phase HPLC [9.4×250 mm Zorbax Sil column, 5 mL/min, 2-propanol/hexane (15:85) solvent system, R$_t$=6.46 min.] and then by reverse phase HPLC [9.4×250 mm Zorbax RX-C18 column, 3 mL/min, methanol/water (85:15) solvent system, R$_t$=10.19 min] to give a colorless oil (12.745 mg, 59% yield):

UV (in EtOH)$\lambda_{max}$ 261.0, 252.0, 244.5 nm; $^1$H NMR (400 MHz, CDCl$_3$) δ6.35 and 5.88 (1H and 1H, each d, J=11.2 Hz, 6- and 7-H), 5.44 (2H, m, 22-H and 23-H), 5.11 and 5.09 (each 1H, each s, =CH$_2$), 4.48 (2H, m, 1β- and 3α-H), 2.84 (1H, dd, J=13.3, 4.4 Hz, 10β-H), 2.80 (1H, br d, J=14.2 Hz, 9β-H), 2.56 (1H, dd, J=13.4, 3.6 Hz, 4α-H), 2.32 (1H, dd, J=13.4, 6.0 Hz, 4β-H), 2.28 (1H, dd, J=13.3, 8.4 Hz, 10α-H), 1.20 (6H, d, J=1.2 Hz, 26,27-H$_6$), 0.95 (3H, d, J=6.6 Hz, 21-H$_3$), 0.528 (3H, s, 18-H$_3$); $^{13}$C NMR (100 MHz) δ151.96 (s, C-2), 143.27 (s, C-8), 141.71 (d, C-22), 130.45 (s, C-5), 124.14 (d, C-6), 122.64 (d, C-23), 115.26 (d, C-7), 107.69 (t, =CH$_2$), 71.76 (d, C-1), 70.75 (s, C-25), 70.60 (d, C-3), 56.54 (d), 56.13 (d), 46.90 (t), 45.80 (s, C-13), 45.74 (t), 40.72 (d), 39.80 (t), 38.11 (t), 29.11 and 29.05 (each q, C-26 and C-27), 28.91 (t), 27.26 (t), 23.24 (t), 22.09 (t), 21.61 (q, C-21), 12.28 (q, C-18); MS (EI) m/z 414 (37, M$^+$), 396 (4, M$^+$-H$_2$O), 381 (1, M$^+$-H$_2$O—CH$_3$), 378 (1, M$^+$-2H$_2$O), 356 (2), 311 (4), 287 (12), 269 (21), 251 (26), 194 (42), 147 (41), 135 (100); exact mass calculated for C$_{27}$H$_{42}$O$_3$(M$^+$) 414.3134, found 414.3142.

Scheme 1

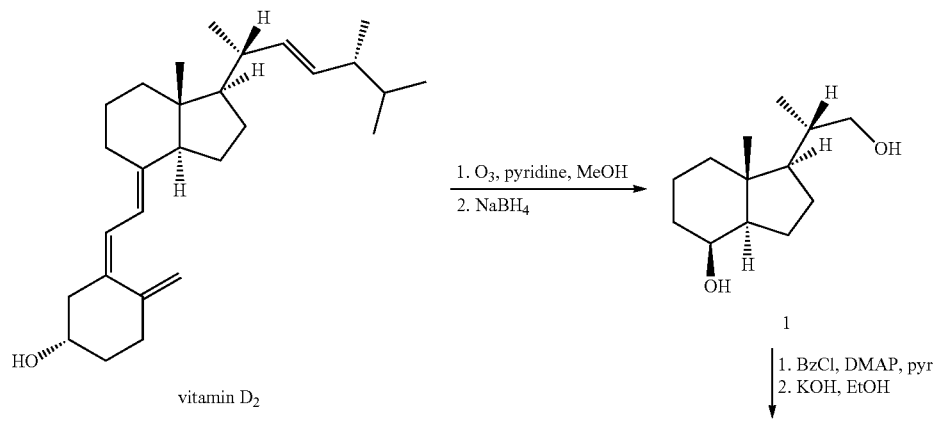

13
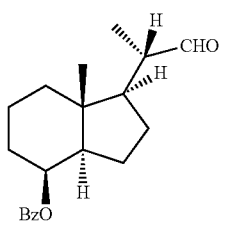
3
14
-continued
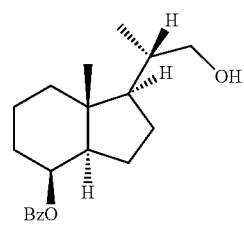
2
SO₃·pyr, Et₃N / DMSO, CH₂Cl₂ ←
1. aq. n-Bu₄NOH, CH₂Cl₂
2. NaBH₄, EtOH
↓
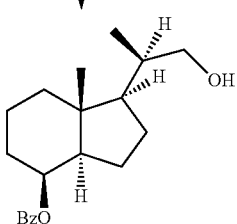
4
SO₃·pyr, Et₃N / DMSO, CH₂Cl₂ →
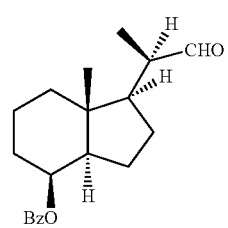
5
n-BuLi, THF | Ph₃P⁺—CH₂CH₂C(CH₃)₂OH Br⁻   6
↓
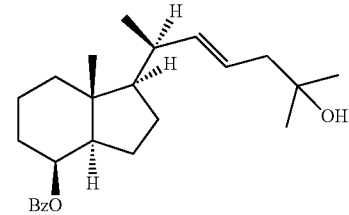
7
Scheme 2
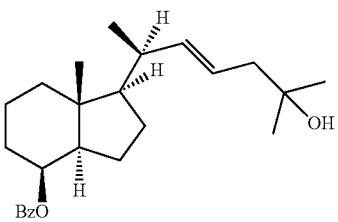
7
TBSOTf, 2,6-lutidine / CH₂Cl₂ →
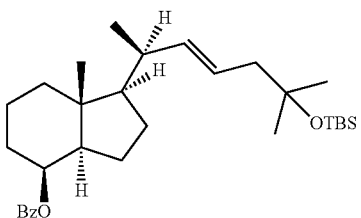
8
↓ NaOH, EtOH
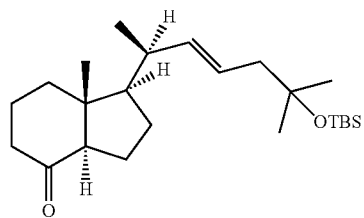
10
← TPAP, NMO / MS 4A, CH₂Cl₂
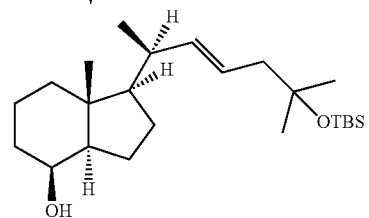
9

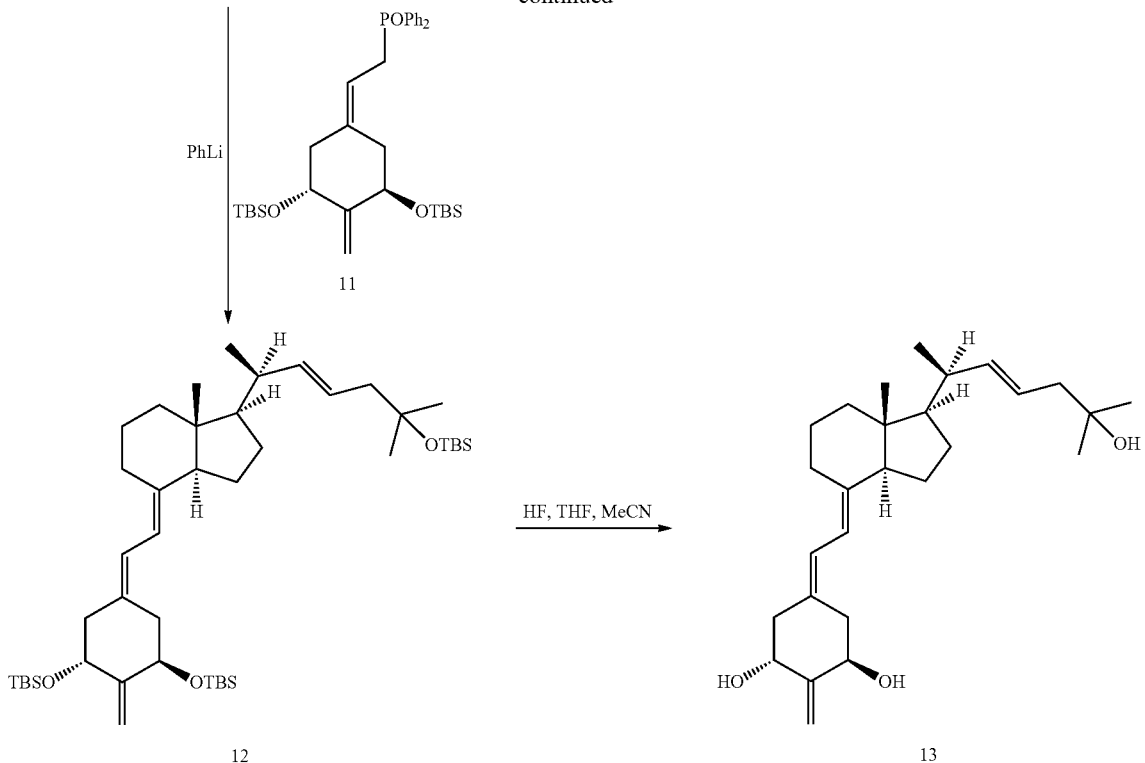

Biological Activity of (20S,22E)-2-methylene-19-nor-22-ene-1α,25-dihydroxyvitamin D₃ Analogs The introduction of a methylene group to the 2-position, as well as a hydroxyl substituent attached to the 25-position (C-25) in the side chain, and having the methyl group normally located at the 21 position (C-21) in the side chain in its epi or S-configuration, and the introduction of a double bond located between carbon atoms 22 and 23 (C-22 and C-23) in the side chain, had little effect on binding of N-23 to the full length recombinant rat vitamin D receptor, as compared to 1α,25-dihydroxyvitamin D₃. The compound N-23 bound with the same affinity to the nuclear vitamin D receptor as compared to the standard 1,25-(OH)₂D₃ (FIG. 1). It might be expected from these results that compound N-23 would have equivalent biological activity. Surprisingly, however, compound N-23 is a highly selective analog with unique biological activity.

Figure 5:
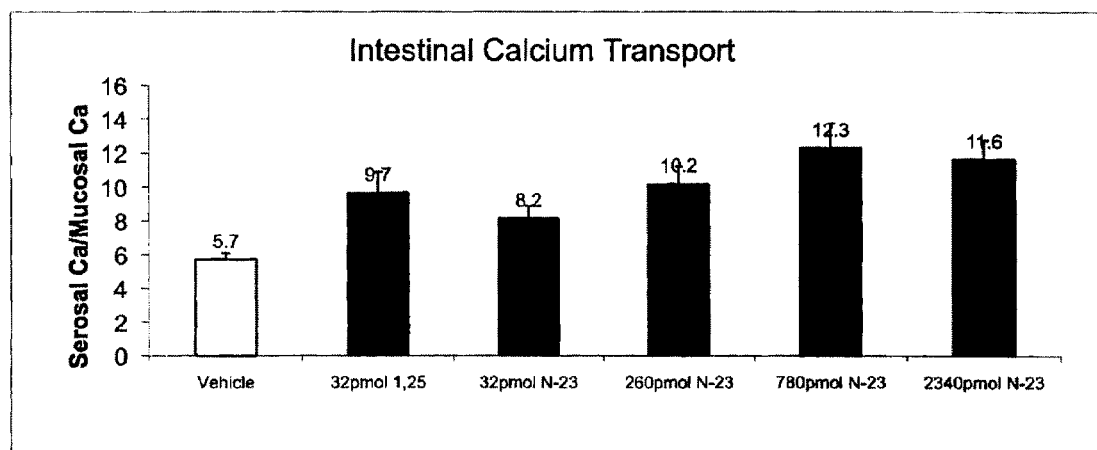

FIG. 5 shows that N-23 has relatively low ability to increase intestinal calcium transport activity in vivo at low dosages. It clearly has lower potency in vivo as compared to that of 1,25-dihydroxyvitamin D₃(1,25(OH)₂D₃), the natural hormone, in stimulating intestinal calcium transport, especially at the recommended lower doses.

Figure 4:
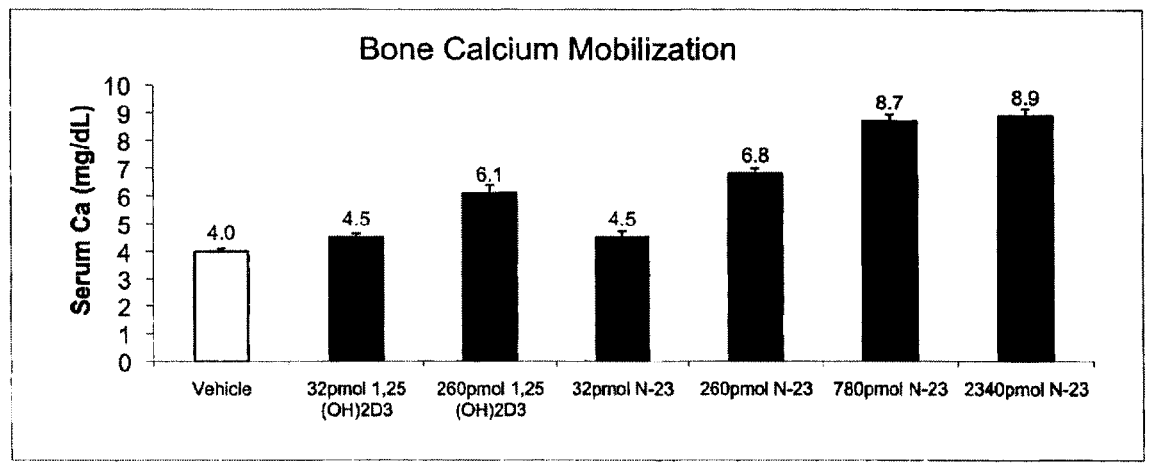

FIG. 4 demonstrates that N-23 has significant bone calcium mobilization activity, as compared to 1,25(OH)₂D₃. N-23 demonstrated slightly more bone calcium mobilization activity than 1,25(OH)₂D₃ (6.8 mg/dL of N-23 versus 6.1 mg/dL of 1,25(OH)₂D₃ at 260 pmol dosage). Thus, N-23 clearly is somewhat more effective in mobilizing calcium from bone as compared to 1,25(OH)₂D₃.

FIGS. 4 and 5 thus illustrate that N-23 may be characterized as being less potent than 1,25(OH)₂D₃ in promoting intestinal calcium transport activity, but being slightly more potent than 1,25(OH)₂D₃ in promoting bone calcium mobilization activity.

Figure 2:
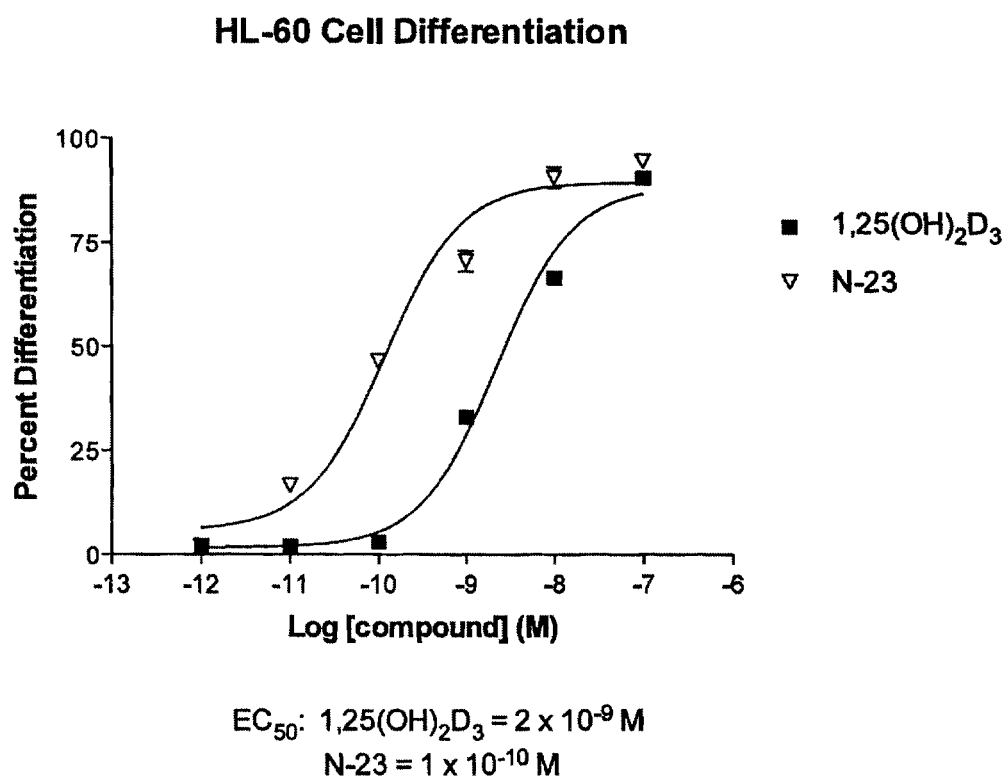

FIG. 2 illustrates that N-23 is about 10 times more potent than 1,25(OH)₂D₃ on HL-60 cell differentiation, i.e. causing the differentiation of HL-60 cells into monocytes. Thus, N-23 may be an excellent candidate for the treatment of a cancer, especially against leukemia, colon cancer, breast cancer, skin cancer and prostate cancer.

Figure 3:
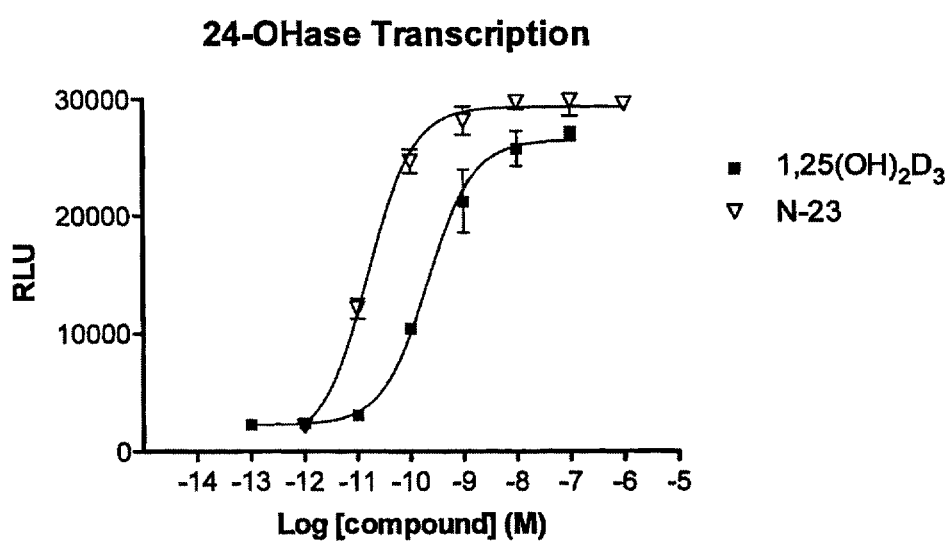

FIG. 3 illustrates that in bone cells the compound N-23 is about 10 times more potent than 1,25(OH)₂D₃ in increasing transcription of the 24-hydroxylase gene. This result, together with the cell differentiation activity of FIG. 2, suggests that N-23 will be very effective in treating the above referred to cancers because it has direct cellular activity in causing cell differentiation, gene transcription, and in suppressing cell growth.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK₅₀ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100, After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet +AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings. This compound N-23 binds the VDR with the same affinity as the native hormone, and can be considered to be equally potent as 1,25(OH)$_2$D$_3$ in this activity. N-23 also displays approximately 10 times more cell differentiation activity and about 10 times more in vitro gene transcription activity compared to 1,25(OH)$_2$D$_3$. While this compound is more potent compared to 1,25(OH)$_2$D$_3$ in vitro, it shows slightly more activity in vivo on bone calcium mobilization compared to the native hormone, and slightly less activity in vivo in promoting intestinal calcium transport compared to the native hormone. N-23 is a potentially valuable compound for therapeutic development as it has higher potency in mobilizing calcium from bone storage and lower potency in stimulating active calcium transport in the gut, but higher potency in cell differentiation potentially resulting in a compound with a bigger safety window than has previously been generated. Because this compound exhibits relatively significant cell differentiation and transcriptional activity, but relatively low calcemic activity on bone, it might be useful for treating patients with various types of cancers, especially for the treatment of leukemia, colon cancer, breast cancer, skin cancer and prostate cancer. N-23 might not only be useful in the treatment of the above listed cancers, but also in the prevention of the above listed cancers.

VDR binding, HL60 cell differentiation, and transcription activity. N-23 ($K_i$=6×10$^{-11}$M) has about the same activity as the natural hormone 1α,25-dihydroxyvitamin D$_3$ ($K_i$=4×10$^{-11}$M) in its ability to compete with [$^3$H]-1,25(OH)$_2$D$_3$ for binding to the full-length recombinant rat vitamin D receptor (FIG. 1), N-23 displays about 10 times more activity (EC$_{50}$=1×10$^{-10}$M) in its ability (efficacy or potency) to promote HL-60 cell differentiation as compared to 1α,25-dihydroxyvitamin D$_3$ (EC$_{50}$=2×10$^{-9}$M) (See FIG. 2). Also, compound N-23 (EC$_{50}$=2×10$^{-11}$M) has about 10 times more transcriptional activity in bone cells than 1α,25-dihydroxyvitamin D$_3$ (EC$_{50}$=2×10$^{-10}$M) (See FIG. 3). These results suggest that N-23 will have significant activity as an anti-cancer agent and will be very effective because it has direct cellular activity in causing cell differentiation, gene transcription, and in suppressing cell growth.

Calcium mobilization from bone and intestinal calcium absorption in vitamin D-deficient animals. Using vitamin D-deficient rats on a low calcium diet (0.02%), the activities of N-23 and 1,25(OH)$_2$D$_3$ in intestine and bone were tested. As expected, the native hormone (1,25(OH)$_2$D$_3$ increased serum calcium levels at all dosages (FIG. 4). The study repotted in FIG. 4 shows that N-23 has significant activity in mobilizing calcium from bone. The administration of 260 pmol/day of N-23 for 4 consecutive days caused mobilization of bone calcium (6.8 mg/dL) and the native hormone 1,25 (OH)$_2$D$_3$ had significant activity at 260 pmol/day where a substantial effect was seen (6.1 mg/dL).

Intestinal calcium transport was evaluated in the same group of animals using the everted gut sac method (FIG. 5). The study reported in FIG. 5 shows N-23 has less intestinal calcium transport activity than 1,25(OH)$_2$D$_3$. Administration of 32 pmol/day of N-23 for 4 consecutive days resulted in less activity as compared to 1,25(OH)$_2$D$_3$ at the same 32 pmol/day dosage.

These results show that the compound N-23 promotes intestinal calcium transport in a dose dependent manner.

Thus, it may be concluded that N-23 has lower intestinal calcium transport activity to that of 1,25(OH)$_2$D$_3$ at the recommended lower doses.

These results further illustrate that N-23 is an excellent candidate for numerous human therapies as described herein, N-23 is an excellent candidate for treating a cancer because: (1) it has significant VDR binding, transcription activity and cellular differentiation activity; (2) it has lower risk of hypercalcemic unlike 1,25(OH)$_2$D$_3$; and (3) it is easily synthesized.

For prevention and/or treatment purposes, the compounds of this invention defined by formula I, particularly N-23, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly N-23, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly N-23, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly N-23, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds I, particularly N-23, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly N-23, may be advantageously administered in amounts sufficient to effect the differentiation of promyelocytes to normal macrophages Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula::

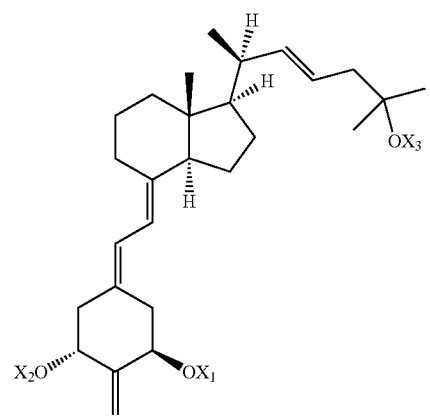

where $X_1$, $X_2$ and $X_3$, which may be the same or different, are each selected from hydrogen or a hydroxy-protecting group.

2. The compound of claim 1 wherein $X_3$ is hydrogen.

3. The compound of claim 1 wherein $X_1$ is hydrogen.

4. The compound of claim 1 wherein $X_1$, $X_2$ and $X_3$ are all t-butyldimethylsilyl.

5. A pharmaceutical composition containing an effective amount of at least one compound as claimed in claim 1 together with a pharmaceutically acceptable excipient.

6. The pharmaceutical composition of claim 5 wherein said effective amount comprises from about 0.01 µg to about 1000 µg per gram of composition.

7. The pharmaceutical composition of claim 5 wherein said effective amount comprises from about 0.1 µg to about 500 µg per gram of composition.

8. A compound having the formula:

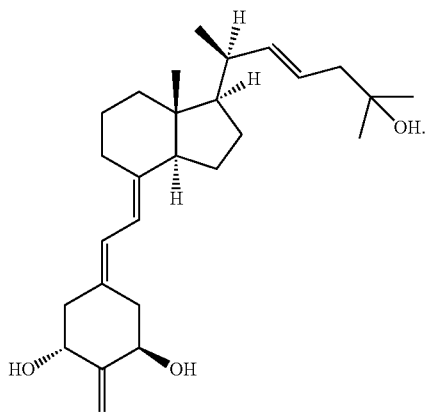

Ia and named (20S,22E)-2-Methylene-19-nor-22-ene-1α,25-dihydroxyvitamin $D_3$.

9. A pharmaceutical composition containing an effective amount of (20S,22E)-2-Methylene-19-nor-22-ene-1α,25-dihydroxyvitamin $D_3$ together with a pharmaceutically acceptable excipient.

10. The pharmaceutical composition of claim 9 wherein said effective amount comprises from about 0.01 µg to about 1000 µg per gram of composition.

11. The pharmaceutical composition of claim 9 wherein said effective amount comprises from about 0.1 µg to about 500 µg per gram of composition, 12. A method of treating a disease selected from the group consisting of leukemia, colon cancer, breast cancer, skin cancer or prostate cancer comprising administering to a subject with said disease an effective amount of a compound having the formula:

I where $X_1$, $X_2$ and $X_3$ which may be the same or different, are each selected from hydrogen or a hydroxyl-protecting group.

13. The method of claim 12 wherein the compound is administered orally.

14. The method of claim 12 wherein the compound is administered parenterally.

15. The method of claim 12 wherein the compound is administered transdermally.

16. The method of claim 12 wherein the compound is administered rectally.

17. The method of claim 12 wherein the compound is administered nasally,

18. The method of claim 12 wherein the compound is administered sublingually.

19. The method of claim 12 wherein the compound is administered in a dosage of from about 0.01 µg/day to about 1000 µg/day.

20. The method of claim 12 wherein the compound is (20S,22E)-2Methylene-19-nor-22-ene-1α,25-dihydroxyvitamin $D_3$ having the formula:

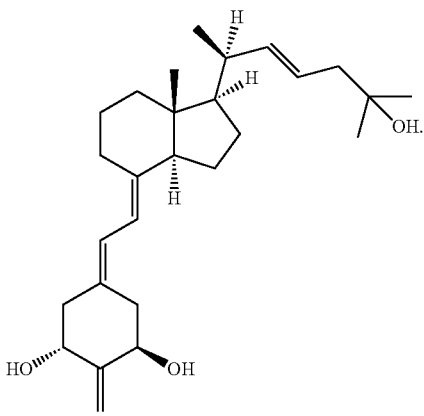

Ia

* * * * *